United States Patent
Ryan et al.

(10) Patent No.: US 9,775,590 B2
(45) Date of Patent: Oct. 3, 2017

(54) BRAIDED HEMOSTASIS SHAFT FOR IMPROVED TORSIONAL RESPONSE

(71) Applicant: Boston Scientific Scimed, Inc., Maple Grove, MN (US)

(72) Inventors: Shawn Ryan, Upton, MA (US); Kevin John Wilcox, Brighton, MA (US); Oliver Gorst, Newton, NJ (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 207 days.

(21) Appl. No.: 14/462,021

(22) Filed: Aug. 18, 2014

(65) Prior Publication Data

US 2015/0057703 A1 Feb. 26, 2015

Related U.S. Application Data

(60) Provisional application No. 61/867,935, filed on Aug. 20, 2013.

(51) Int. Cl.
*A61B 17/00* (2006.01)
*A61B 17/12* (2006.01)
(Continued)

(52) U.S. Cl.
CPC ...... *A61B 17/0057* (2013.01); *A61B 17/1285* (2013.01); *A61B 17/12145* (2013.01); *A61B 17/29* (2013.01); *A61B 10/06* (2013.01); *A61B 2017/0034* (2013.01); *A61B 2017/00296* (2013.01); *A61B 2017/00305* (2013.01); *A61B 2017/00592* (2013.01); *A61B 2017/12004* (2013.01); *A61B 2017/1205* (2013.01); *A61B 2017/2905* (2013.01); *A61B 2090/037* (2016.02)

(58) Field of Classification Search
CPC ... A61B 1/005; A61B 1/0055; A61B 1/00071; A61B 17/0057; A61B 17/12145; A61B 1/0051; A61B 17/1285; A61B 17/29
See application file for complete search history.

(56) References Cited

U.S. PATENT DOCUMENTS 4,945,920 A  8/1990 Clossick
5,788,714 A * 8/1998 Ouchi ............... A61B 1/00071
                                            138/123

(Continued)

FOREIGN PATENT DOCUMENTS

EP  2 213 325  8/2010
EP  2 450 077  5/2012

(Continued)

*Primary Examiner* — Tuan V Nguyen
(74) *Attorney, Agent, or Firm* — Fay Kaplun & Marcin, LLP

(57) ABSTRACT

A medical insertion device includes an elongated shaft extending from a proximal end to a distal end and having flexibility sufficient for insertion through a working channel of an endoscope along a tortuous path. The elongated shaft includes a coil extending from the proximal end to the distal end and having a channel extending longitudinally therethrough and a braided portion extending around a portion of the coil, the braided portion including a plurality of lines wound together such that first and second ones of the lines intersect to enclose a predetermined angle therebetween, the angle being between 25 and 55 degrees.

17 Claims, 5 Drawing Sheets

(51) Int. Cl.
*A61B 17/128* (2006.01)
*A61B 17/29* (2006.01)
*A61B 10/06* (2006.01)
*A61B 90/00* (2016.01)

(56) References Cited

U.S. PATENT DOCUMENTS

| | | |
|---|---|---|
| 6,520,214 B1 | 2/2003 | Sugiyama et al. |
| 6,554,820 B1 | 4/2003 | Wendlandt et al. |
| 6,689,120 B1 * | 2/2004 | Gerdts ............... A61M 25/005 604/526 |
| 2008/0097152 A1 * | 4/2008 | Stefanchik ......... A61B 1/00071 600/114 |
| 2008/0262472 A1 * | 10/2008 | Lunn ................ A61M 25/0012 604/527 |
| 2008/0306491 A1 * | 12/2008 | Cohen ................ A61B 17/122 606/142 |
| 2011/0196418 A1 | 8/2011 | Castro |
| 2012/0179171 A1 | 7/2012 | Cohen et al. |

FOREIGN PATENT DOCUMENTS

| | | |
|---|---|---|
| JP | 2007-082802 | 4/2007 |
| JP | 2009-117410 | 5/2009 |
| JP | 2010-005430 | 1/2010 |
| JP | 2011-506369 | 3/2011 |
| JP | 2012-196275 | 10/2012 |

\* cited by examiner

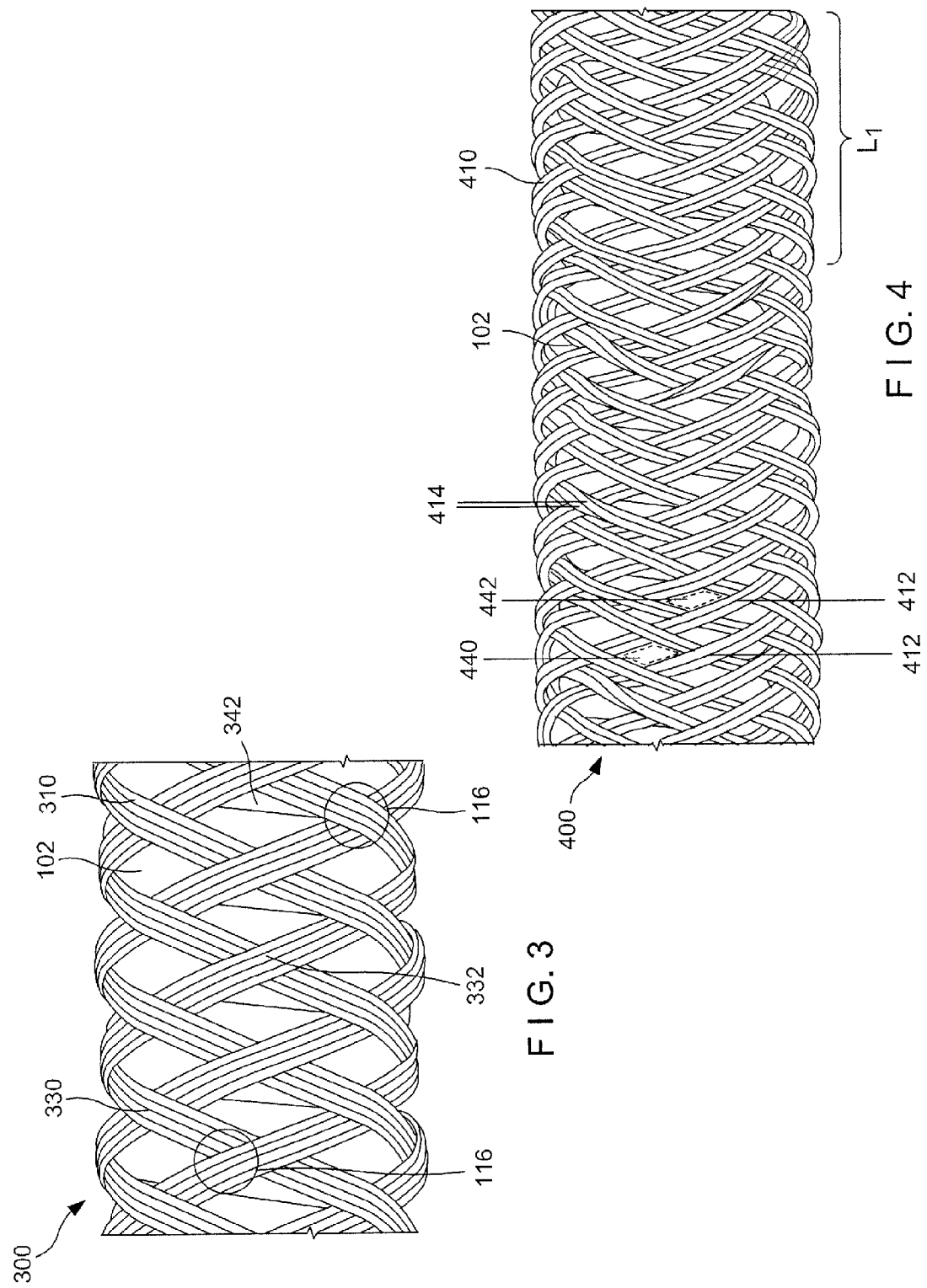

BRAIDED HEMOSTASIS SHAFT FOR IMPROVED TORSIONAL RESPONSE

PRIORITY CLAIM

The present application claims priority to U.S. Prov. Appln. Ser. No. 61/867,935 filed Aug. 20, 2013. The entire specification of the above application is incorporated herein by reference.

BACKGROUND

Pathologies of the gastro-intestinal ("GI") system, the biliary tree, the vascular system and other body lumens are commonly treated through endoscopic procedures, many of which require active and/or prophylactic hemostasis to control internal bleeding. Tools for deploying hemostatic clips via endoscopes are often used to control internal bleeding by clamping together the edges of wounds or incisions. These tools are inserted into the body through a working channel of an endoscope. Specifically, the tools may be attached to an elongated coil inserted through the endoscope to provide the flexibility necessary to permit insertion through a tortuous path in the body. However, elongated coils often do not provide torsional stiffness sufficient to translate a desired rotation imparted to the proximal end of the coil (e.g., at a proximal handle) to the hemostasis device (e.g., clip, etc.) coupled to the distal end of the coil. Specifically, as coils compress or expand when subjected to a twisting load until an outside diameter of the spring meets an opposing force, much of the energy input into the coil is dissipated before being transmitted to the distal end of the coil. Thus, a significant portion of rotation applied to a proximal end of a coil causes expansion/compression of the coil and does not translate in a corresponding rotation at the distal end thereof.

SUMMARY

The present disclosure relates to a medical insertion device comprising an elongated shaft extending from a proximal end to a distal end and having flexibility sufficient for insertion through a working channel of an endoscope along a tortuous path. The elongated shaft includes a coil extending from the proximal end to the distal end and having a channel extending longitudinally therethrough and a braided portion extending around a portion of the coil, the braided portion including a plurality of lines wound together such that first and second ones of the lines intersect to enclose a predetermined angle therebetween, the angle being between 25 and 55 degrees.

BRIEF DESCRIPTION OF THE DRAWINGS

FIG. 3 shows a perspective view of a shaft according to a second alternate embodiment of the disclosure;

FIG. 4 shows a perspective view of a shaft according to a third alternate embodiment of the disclosure;

DETAILED DESCRIPTION

Figure 1:
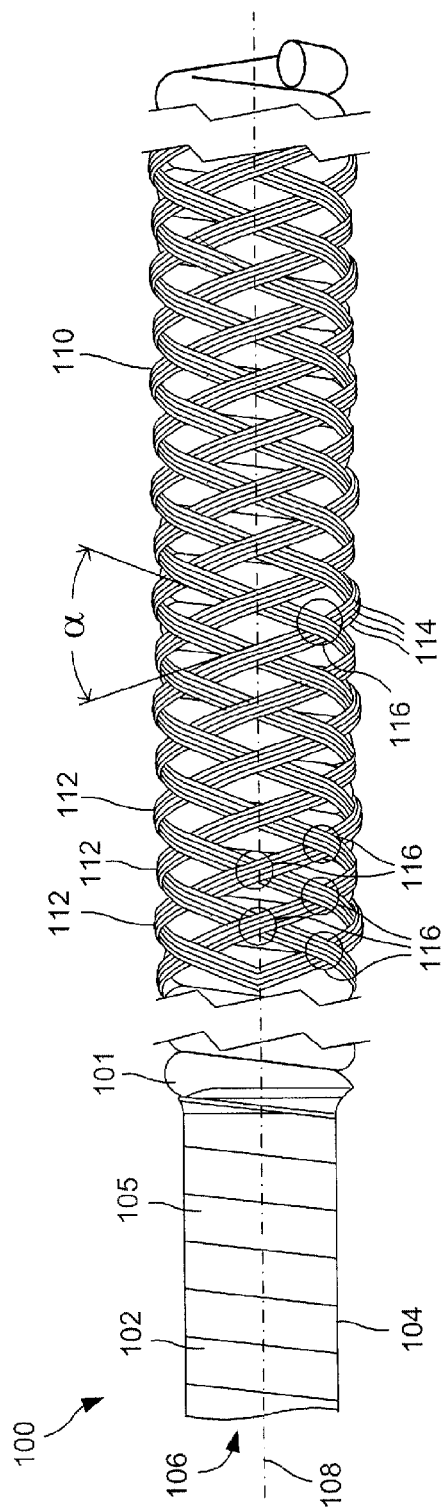
FIG. 1 shows a perspective view of a shaft according to a first exemplary embodiment of the present disclosure.

The present disclosure may be further understood with reference to the following description and the appended drawings, wherein like elements are referred to with the same reference numerals. The present disclosure relates to a flexible shaft for permitting the transmission of rotation applied to a proximal end of the shaft to a corresponding rotation of the distal end of the shaft so that this rotation may effect a device coupled to the distal end of the shaft when that device has been inserted into the body along a tortuous path to, for example, perform hemostasis. It is noted, however, that the exemplary shaft according to the disclosure may be used with devices used to perform any endoscopic procedure including, but not limited to band ligation, injection therapy, thermal electrohemostasis, combination therapy needle, biopsies, fine-needle aspiration and procedures for the treatment of the upper and lower gastrointestinal ("GI") tract. The exemplary shaft according to the disclosure comprises an elongated coil pre-wound with a predetermined diameter, length, number of turns, etc., as will be described in greater detail later on. The shaft further comprises a braided element wound over the coil, the braided element formed as a predetermined plurality of wires wound together in a predetermined pattern relative to one another, as will also be described in greater detail later on. A braid angle of wires comprising the braid is selected to enclose an angle including or within 25-55 degrees. As will be described in greater detail later on, this range provides the shaft with the required torsional stability to transmit rotation to the device coupled to the distal end of the shaft while still permitting the shaft to flex to permit insertion thereof through the tortuous anatomy. It should be noted that the terms "proximal" and "distal," as used herein, are intended to refer to a direct toward (proximal) and away from (distal) a user of the device.

As shown in FIG. 1, a device 100 according to an exemplary embodiment of the disclosure includes an elongated body 101 extending longitudinally from a proximal end (not shown) accessible to a physician or other user in an operative configuration to a distal end (not shown) which, in use, is inserted into a living body to a site adjacent to target tissue. The device comprises a first portion 102 formed as a coil, the coil comprising an elongated wire or filament 104 wound to a coiled configuration and having a predetermined spring constant, as those skilled in the art will understand. The first portion 102 is sized to permit insertion thereof into a working channel (not shown) of an endoscope (i.e., with an outer diameter of the device 100 being less than an inner diameter of the working channel). A lumen 106 extends through the device 100 along a longitudinal axis 108 thereof. In an exemplary embodiment, the first portion 102 is formed of a single wire or filament 104 wound into the configuration of FIG. 1. It is noted however, that any number and arrangement of wires 104 may be employed herein without deviating from the scope of the disclosure. For example, the first portion 102 may comprise multiple coils provided over one another, with each of the coils being wound in an opposing direction relative to an adjacent one of the coils.

A second portion 110 of the device 100 is formed as a braided outer portion enveloping the first portion 102. The second portion 110 comprises a plurality of lines or wires 112 wound together in a braided arrangement over the coiled first portion 102. The exemplary embodiment of FIG. 1 depicts eight lines or carriers 112. It is noted, however, that any number of lines may be employed without deviating from the scope of the disclosure. In an exemplary embodiment, each of the lines 112 comprises four individual strands 114 such that a total of 32 strands form the second portion 110. It is noted, however, that each line 112 may include any number of filaments without deviating from the scope of the disclosure, wherein the number of filaments 114 used may depend on an outer diameter of each filament 114. For example, each line 112 may comprise any of one, two, three, four, five or more individual strands 114, as will be described in greater detail in later embodiments.

Furthermore, each of the lines 112 may include a different number of individual strands 114 to affect an overall stiffness of the second portion 110 and, consequently, the device 100, as those skilled in the art will understand and as will also be described in greater detail in later embodiments. In another embodiment, the braided second portion 110 may be unbalanced to simulate dual coils formed with opposing windings, as those skilled in the art will understand. For example, the braided second portion 110 may comprise a first line 112 formed with one or more strands 114 having first diameter wound with a second line 112 formed one or more strands 114 having a second diameter different from the first diameter. In an exemplary embodiment, the diameter of a plurality of individual strands 114 forming a line 112 is substantially the same. The strands 114 according to this exemplary embodiment have a substantially circular cross-section although any other cross-sectional shape may be used without deviating from the scope of the disclosure, including, but not limited to rectangular and oval.

The lines 112 are braided with a predetermined braid angle relative to one another. As shown in FIG. 1, the lines 112 intersect one another at crossing 116. Portions of the lines 112 extending away from each of the crossings are angled to enclose an angle α therebetween. In a first exemplary embodiment, the angle α is 40.5°. In another exemplary embodiment, the angle α is 37.5°. In yet another exemplary embodiment, the angle α may be any angle including and between 25°-55°. The exemplary braid angle α is selected to provide a proper balance of bending and torsional stiffness for the device 100 to perform in a tortuous path. Specifically, the present disclosure establishes that a braid angle of approximately 55° or greater increases the bending stiffness to a level above that suited for bending through a tortuous path. The present disclosure further establishes that a braid angle of less than 25° does not provide enough torsional stiffness to transmit rotation along the coil when it is bent along a tortuous path. The exemplary range according to the disclosure provides a balance of torsional stiffness and rotational transmittal to permit insertion of the device 100 through a tortuous path while transmitting rotation imparted to a proximal end of the coil along the coil to a distal end thereof. However, in applications where low tortuosity is to be encountered, a braid angle=55° may be used. Similarly, in applications where high tortuosity is encountered, a braid angle=25° may be used.

It is noted that, although the embodiment of FIG. 1 is depicted with a uniform braid angle α throughout its length, the braid angle α may be modified in different portions of the device 100 without deviating from the scope of the disclosure. Although, braid angles of less than 25° and greater than 55° are unsuitable for use along the majority of the length of these coils, small portions of the coils that require either extra flexibility or increased stiffness may be formed with braid angles outside the range. For example, a first section of the length of the second portion 110 adjacent to a distal tip of the device 100 may be formed with a braid angle α less than 25° for increased flexibility, the first section having a high pick count. The length of the first section is dependent on the specific application (e.g., tortuosity of target anatomy). As the tortuosity of the anatomy increases, the deflectability of the first section decreases to achieve a desired torsional/rotational performance. In another embodiment, instead of providing a first section with a braid angle α of less than 25°, the braid may be omitted in this region to further increase flexibility of the first portion 102. In one exemplary embodiment, the first section may extend up to 15.24 cm from the distal end of the first portion 102. Similarly, a second section of the second portion 110 may be formed with a braid angle α greater than 55° when additional stiffness is required. Similar to the first section, a length of the second section is dependent on a tortuosity of the target anatomy as well as other factors including, but not limited to, a length of the first portion 102 which will remain outside of the endoscope during the procedure, desired stroke length during insertion into the working channel of the endoscope, etc. For example, the length of the second section may be larger when used with an upper gastrointestinal (GI) endoscope since the distance between the proximal handle of the endoscope and the entry port of the endoscope is substantially large when compared to procedures for other portions of the anatomy. In another embodiment, the second section may be positioned near the proximal end of the second portion so that it remains outside of any tortuous anatomy in an operative configuration.

The torsional stability and bending stiffness of the second braided portion 110 may also be modified by changing a pick count thereof. The pick count refers to the number of braid crossings formed over a unit length of the coil. In an exemplary embodiment, as shown in FIG. 1, the pick count may comprise 17 crossings per a unit length of 10 mm. It is noted, however, that any other pick count may be used without deviating from the scope of the disclosure. As those skilled in the art will understand, the pick count varies according to the number of individual filaments 114 forming the braided second portion 110, the number of lines 112 and the type of braid pattern selected.

The exemplary braided second portion 110 in the exemplary embodiment is formed of a biocompatible material such as stainless steel, or other biocompatible metals and alloys, biocompatible polymers, plastic coated wire or a hybrid of materials. In one embodiment, each of the individual strands 114 is formed with a plastic coating which may be reflowed (e.g., by heating) to lock the braided second portion 110 in a desired configuration. Proximal and distal ends of the braided second portion 110 may be tapered to lie flush against the first portion 102. This taper may be formed in the lines 112 or may be machined after braided (e.g., by grinding, etc.).

The device 100 may be formed such that the first portion 102 includes a reduced diameter portion 105 at a distal end thereof. As those skilled in the art will understand, this configuration provides added flexibility in the distal end of the device to, for example, aid in traversal of the device 100 through a tortuous path in the body. The reduced diameter portion 105 may be provided at one or more of a distal end of the body 101, proximal end of the body or at any position therebetween. In an exemplary embodiment, the reduced diameter portion 105 is ground down to have a diameter smaller than that of outlying sections of the first portion 102. It is noted that, due to the added flexibility imparted by the reduced diameter portion 105, this portion may not include the second portion 110 extending thereover. In such an embodiment, the second portion may terminate at a location proximal to the reduced diameter portion 105. Lines 112 comprising the second portion 110 may gradually taper down in diameter at the termination to prevent damage to the working channel of the endoscope. In another embodiment, the first portion 102 has a diameter uniform along its length, with the second portion 110 terminating proximally of a distal end of the first portion 102 to increase flexibility at the distal end. In yet another embodiment, the first portion 102 may be fitted with a plurality of second portions 110 over a length thereof, the plurality of second portions 110 being separated from one another to define regions of increased flexibility along the length of the device 100.

Figure 8:
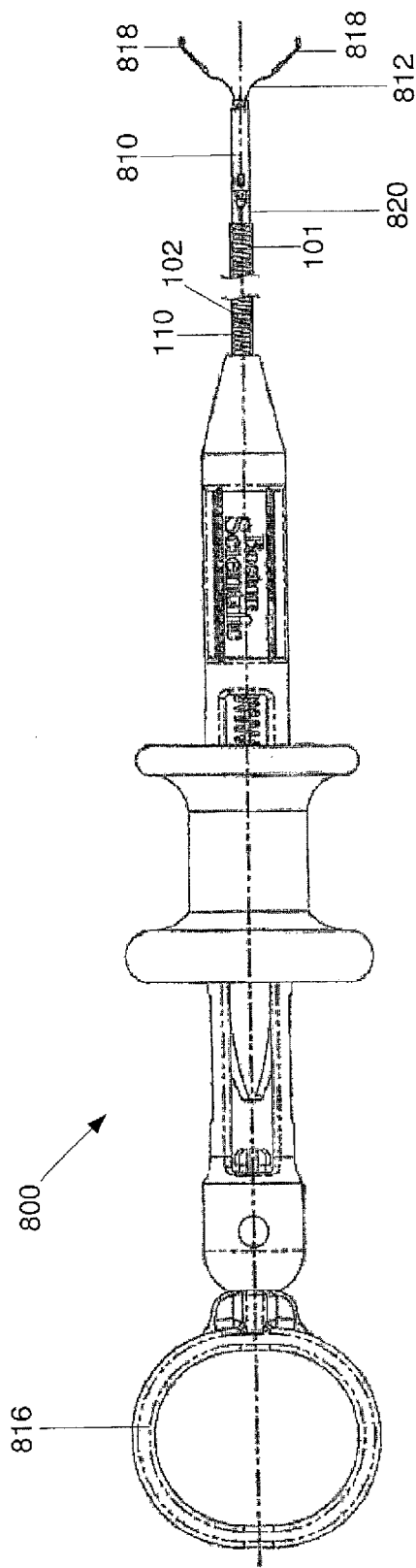
FIG. 8 shows a perspective view of a clipping device fitted with the exemplary shaft of FIG. 1.
Figure 9:
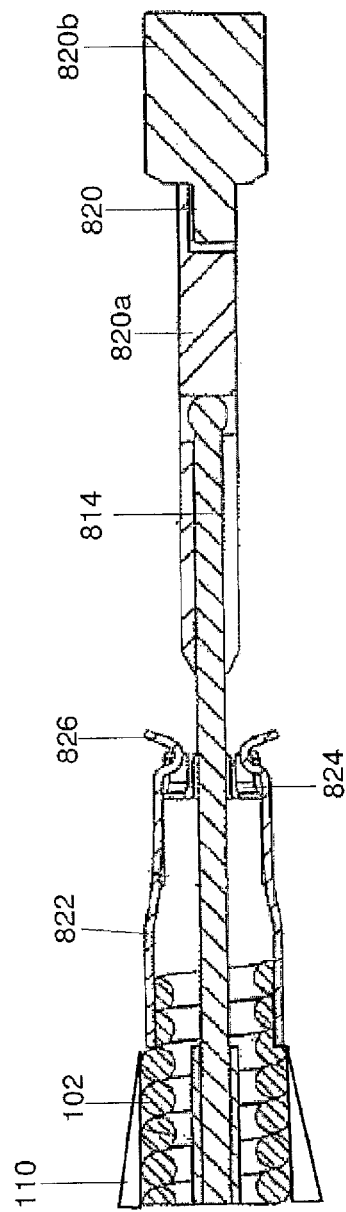
FIG. 9 shows a partial cross-sectional view of the clipping device of FIG. 8.

As shown in FIG. 8, the exemplary device 100 may be used in a clipping apparatus 800. The clipping apparatus 800 includes a cylindrical capsule 810 releasably coupled to a distal end of a the elongated body 101 of the device 100. As described in greater detail earlier, an outer diameter of the second portion 110 of the device 100 may gradually taper toward the distal end of the elongated body 101. The capsule 810 receives the proximal end of a single hemostatic clip 812. The clip 812, which is coupled via a control wire 814 to a proximal actuating handle 816 remaining outside the body, includes a pair of tissue gripping arms 818 for bringing together separated portions of tissue (e.g., to close a wound). As with closure devices generally, the clip 812 is designed to be left in place after a procedure has been completed to hold together the edges of tissue while natural healing processes knit them together. When this process has progressed sufficiently that the tissue can hold itself together without assistance from the clip 812, the clip 812 may be removed (e.g., through a separate procedure) or may be left in place to be sloughed off naturally as the gripped tissue is shed.

In an operative configuration, the elongated body 101 is inserted into a living body (e.g., after being passed through a natural body orifice along a tortuous path) so that a distal end thereof is positioned adjacent a target location. At this desired position, the clip 812 is moved distally out of the capsule 810 so that the arms 818 spread apart into the tissue-receiving configuration under their natural bias. At any time prior to or after advancing the clip 812 out of the capsule 810, rotation may be applied to a proximal end of the elongated body 101 to rotate the capsule 810 and clip 812 to orient the arms 818 as desired relative to the target tissue. The control wire 814 is then actuated to draw the clip 812 proximally into the capsule 810 closing the clip arms 818 over the target tissue. When drawn into the capsule 810 to this maximum proximal extent, the capsule 810 constrains the arms 818 to remain in a closed position with the distal ends of the arms 818 drawn together. At this point, additional proximal force applied to the control wire 814 increases tension on the control wire until a predetermined tension is reached at which a joint between two parts, 820a, 820b of a core member 822 coupled between the control wire 814 and the clip 812 fails. This releases the capsule 810 and the clip 812 from the elongated body 101 and locks the clip 812 in the closed position over the clipped tissue.

The capsule 810 in this exemplary embodiment is removably connected to the elongated body 101 by a bushing 822. As the severed proximal portion 820a of the core member 820 is drawn proximally out of the capsule 810, it pushes a bushing support 824 out of engagement with tabs 826 connecting the bushing 822 to the capsule 810 thereby detaching the capsule 810 from the elongated body 101. That is, when the bushing support 824 is moved out of a position in which it supported the tabs 826 in a radially outward position, the tabs 826 spring radially inward out of engagement with corresponding windows in the proximal end of the capsule 810. This separates the capsule 810 from the bushing 822 attached to the elongated body 101, allowing the apparatus 800 to be withdrawn from the body while leaving the clip 812 in place over the target tissue.

Figure 2:
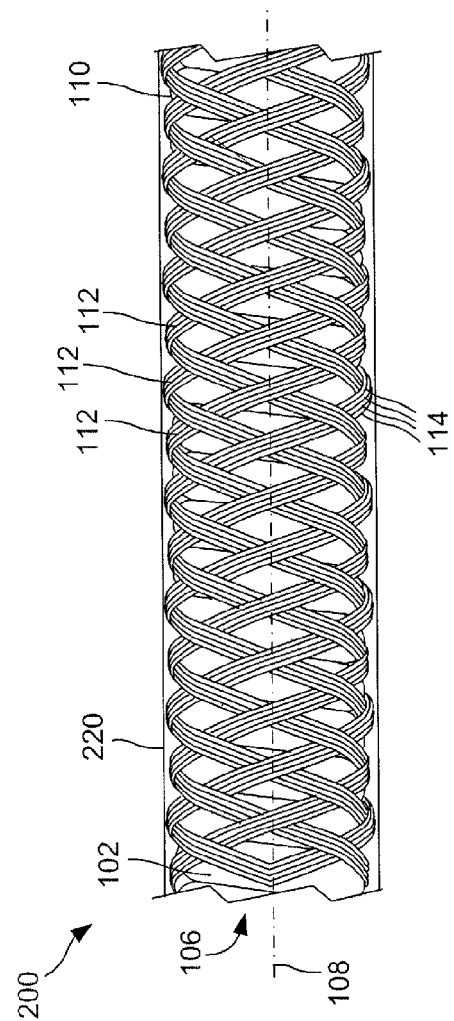
FIG. 2 shows a perspective view of a shaft according to a first alternate embodiment of the disclosure.

As shown in FIG. 2, a device 200 according to an alternate embodiment of the disclosure is substantially similar to the device 100 and like elements have been referenced with like reference numerals, except as noted below. The device 100' comprises a plastic extrusion 220 formed over the braided second portion 110. The plastic extrusion 220 is positioned over the braided second portion 110 and reflowed (e.g., by heating) to lock the braided second portion 110 in a desired configuration over the first portion 102. In another embodiment, the plastic extrusion 220 may be positioned between the first and second portions 102, 110 and subsequently reflowed (e.g., via heating) to move the device 200 to a locked configuration in which the first and second portions 102, 110 are not movable relative to one another. By providing the plastic extrusion 220 over an outer surface of the braided second portion 110, a protective coating is provided to shield the working channel (not shown) of the endoscope (not shown) from damage while also preventing/minimizing kinking of the device 200 as it is inserted through the working channel, as those skilled in the art will understand. The exemplary plastic extrusion 220 may be formed as a heat shrink tube.

FIG. 3 depicts a device 300 according to another embodiment of the disclosure, wherein the device 300 may be moved to a locked configuration without the use of a plastic extrusion. The device 300 is substantially similar to the device 100 and like elements have been referenced with like reference numerals, except as noted below. Specifically, the braid pattern design of a braided second portion 310 may be formed to lock over the first portion 102 by using a locking pattern of braid along a single section, multiple sections or the entire length of the device 100. That is, crossings 116 of lines 312 of the device 300 interlock with the peaks and valleys formed by the wound wire 104 forming the coiled first portion 102. The braid crossings may be formed such that some crossings 330 occur in valleys 340 of the coiled first portion 102 and other crossings 332 occur in peaks 342 of the coiled first portion 102. The crossings may be formed to occur in one of the peaks, valleys or a combination of the two, as shown in FIG. 3 to lock the second portion 310 to the coiled first portion 102. This configuration may be used to simulate a rip-stop style fabric such that the second portion 310 is resistant to unwinding or other damage. If a section of the second portion 310 is damaged, the exemplary construction will prevent the damage from spreading to other parts of the second portion. Furthermore, the exemplary construction disclosed above assists in distributing stress loads on the individual crossings 330, 332 to further prevent the application of a strain that may lead to a breakage thereof.

In an exemplary embodiment, the device 300 is formed with four lines or carriers 310, each including four strands 112. It is noted, however, that any variation in the number of lines 310 and strands 112 per line may be used without deviating from the scope of the disclosure.

In yet another embodiment, the second portion 110, 210, 310 may be locked in position via a mechanical treatment including, but not limited to, crimping, welding and swaging the second portion 110, 210, 310 to the first portion 102.

Figure 5:
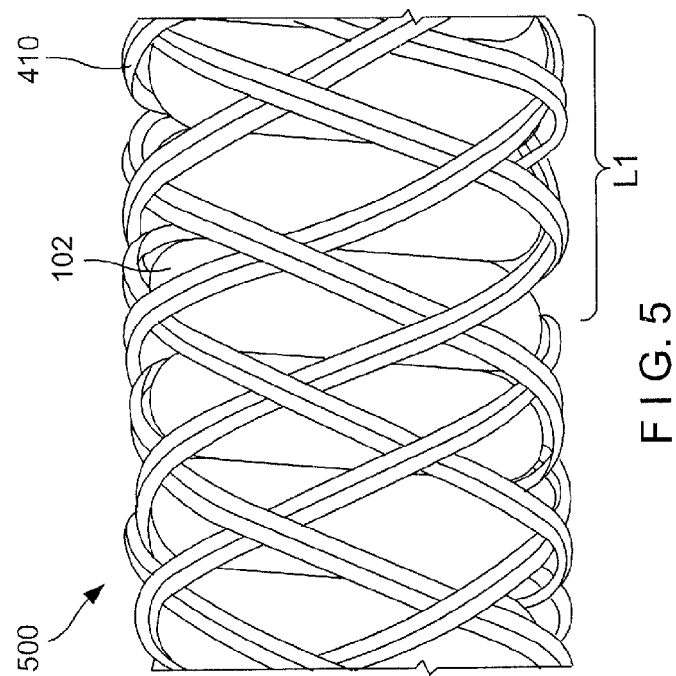
FIG. 5 shows a perspective view of a shaft according to a fourth alternate embodiment of the disclosure.

FIG. 4 depicts a device 400 according to another embodiment of the disclosure. The device 400 is formed substantially similar to the device 100, except as noted below. The device 400 comprises a braided second portion 410 formed of groups of lines 412 each comprising two filaments 414. A pick count of the second portion 410 over a length L1 may be greater than the pick count of the device 100 to provide increased stiffness to the device 400. The pick count may be selected to conform to the requirements of a particular procedure and may vary along a length of the device 400. As shown with respect to the device 500 of FIG. 5, the pick count may be decreased over the length L1, resulting in a corresponding increase of the angle α.

The second portion 410 is formed with a braid pattern selected so that a first negative space 440 (i.e., the substantially diamond shape opening) formed between a first set of adjacent lines 412 has a different size than a second negative space 442 formed between a second set of adjacent lines 412. This pattern is imparted to the second portion 410 during a braiding process. This pattern allows for longitudinal expansion and compression of the device 400 during use, thus aiding in insertion of the device 400 into the body. In the present embodiment, the first negative space 440 is originally larger than the second negative space 442. It is further noted that the braid may be formed to having any number of negative spaces 440, 442 having different dimensions to impart a desired flexibility to the device 400. Furthermore, the braid may be patterned so that only a predetermined length thereof includes the different dimensions of the negative spaces. For example, in one non-limiting example, only a distal tip of the device 400 may include the negative spaces having different dimensions. The exemplary features of the device 400 may further be used in combination with any of the other features disclosed herein to impart a desired flexibility to select portions of the device. It is noted that the braid patterns disclosed above is exemplary only and variations thereof are envisioned within the scope of the disclosure.

Figure 6:
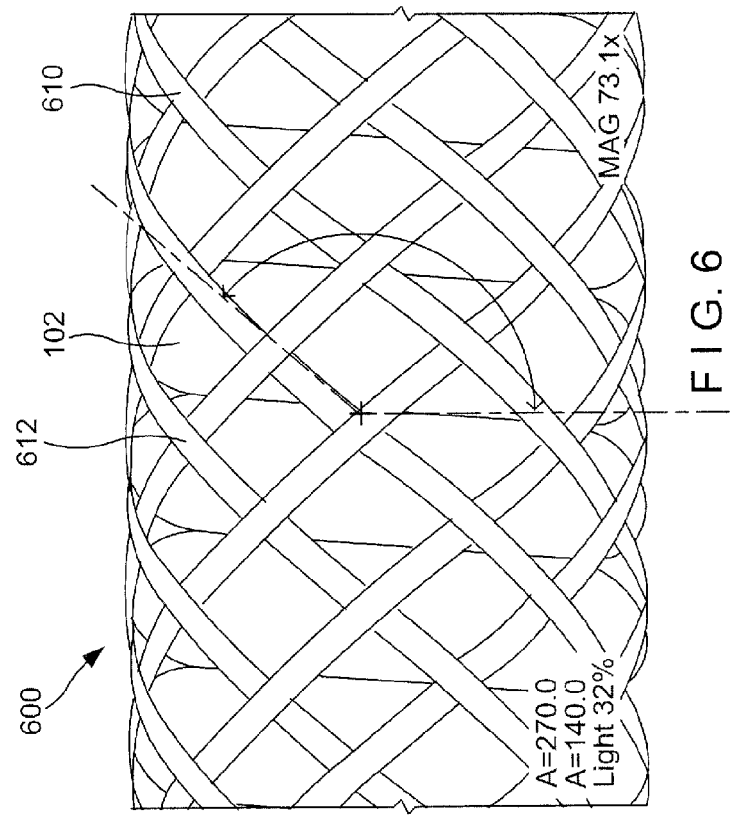
FIG. 6 shows a perspective view of a shaft according to a fifth alternate embodiment of the disclosure.

As shown in FIG. 6, a shaft 600 according to yet another embodiment of the disclosure is substantially similar to the shaft 100 except as noted below. The shaft 600 includes a plurality of single wires or strips 612 braided together. Each of the single wires 612 is formed with a flat, substantially rectangular cross-section. It is noted however, that any other cross-sectional shape may be used without deviating from the scope of the disclosure including, but not limited to circular and oval.

Figure 7:
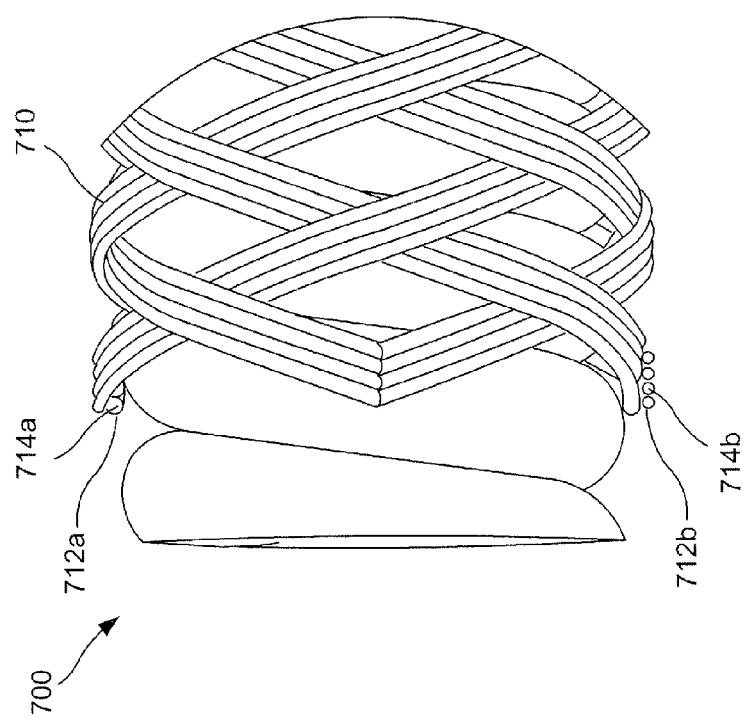
FIG. 7 shows a perspective view of a shaft according to a sixth alternate embodiment of the disclosure.

FIG. 7 depicts a device 700 according to another embodiment of the disclosure. The device 700 is formed substantially similar to the devices discussed earlier, except as noted below. A second portion 710 of the device 700 comprises a first line 712a having strands 714a of a first diameter, the first and second lines 712a, 712b being braided to form an unbalanced braid pattern. The second portion 710 also comprises a second line 712b having strands 714b of a second diameter smaller than the first diameter. That is, each of the four strands 714a of the first line 712a all have the same first diameter while each of the four strands 714b of the second line 712b all have the same second diameter. The consequence of this structure is that, while braiding the first and second lines 712a, 712b a tension on each of the lines is altered to increase and decrease tension in respective portions of the second portion 710. Specifically, as those skilled in the art will understand, a tension on the larger diameter first line 712a will be greater than a tension of the second line 712b. In another embodiment, the unbalanced braid may be achieved by braiding the first line 712a in a clockwise direction while braiding the second line 712b in a counter-clockwise direction. This type of unbalanced braid may be formed of first and second lines 712a, 712b having the same diameter or different diameters. It is noted that although the device 700 has been described with first and second lines 712a, 712b, any number of lines may be used in the device 700 without deviating from the scope of the disclosure.

The exemplary embodiments of the disclosure permit the application of an external rotation to the devices 100-700, wherein the entire device 100-700 may be rotated to impart a corresponding rotation to a mechanism (e.g., a clipping device) attached to a distal end thereof. A surgeon or other user may impart this rotation with or without the use of a handle provided on a proximal end of the device. In contrast, a control wire mechanism, as used in current devices requires the use of a handle in order to impart rotation to a mechanism coupled thereto. The exemplary external rotation of the devices 100-700 according to the disclosure provide the further advantage of transmitting rotation without bowing or winding up. Specifically, control wire based rotation mechanisms are subject to winding up during rotation and causing a whipping and uncontrolled movement of the distal end thereof. The exemplary devices are formed to prevent such a winding or bowing and are capable of transmitting rotation effectively and precisely.

The exemplary braided second portion according to the disclosure may be formed over the coiled first portion during manufacture and may be formed via a knit or crochet pattern.

It will be understood by those of skill in the art that individual features of the embodiments described above may be omitted and or combined to form alternate embodiments. Furthermore, it will be understood by those skilled in the art that various modifications can be made in the structure and the methodology of the present disclosure, without departing from the spirit or scope of the disclosure. For example, although the present disclosure has been described with respect to a clipping device, the exemplary system and method may also be used to perform biopsy procedures or any other medical procedure wherein improved rotation of a component is required in combination with a function of opening/closing a device, extending/retracting a device into tissue, etc., as those skilled in the art will understand. It is therefore respectfully submitted that the exemplary shaft according to the disclosure may be employed with and within any other medical device requiring precise rotational control without deviating from the spirit and scope of the disclosure. Thus, it is intended that the present disclosure cover the modifications and variations of this disclosure provided that they come within the scope of the appended claims and their equivalents.

What is claimed is:

1. A medical insertion device, comprising:
an elongated shaft extending from a proximal end to a distal end and having flexibility sufficient for insertion through a working channel of an endoscope along a tortuous path, the elongated shaft including:
a coil extending from the proximal end to the distal end and having a channel extending longitudinally therethrough; and
a braided portion extending around a portion of the coil, the braided portion including a plurality of lines wound together such that first and second ones of the lines intersect to enclose a predetermined angle therebetween, the angle being at least 25 degrees and less than 50 degrees, wherein each of the first and second ones of the lines includes at least one filament, a diameter of the filaments of the first one of the lines being different from a diameter of the filaments of the second one of the lines.

2. The medical insertion device of claim 1, wherein the first one of the lines includes one of one, two, three and four filaments and the second one of the lines includes one of one, two, three and four filaments.

3. The medical insertion device of claim 2, wherein each of the lines contains the same number of filaments.

4. The medical insertion device of claim 1, wherein the braided portion includes eight lines wound together.

5. The medical insertion device of claim 1, further comprising a plastic extrusion on the braided portion to lock an orientation of the braided portion relative to the coil.

6. The medical insertion device of claim 5, wherein the plastic extrusion is positioned on one of an outer surface of the braided portion and an inner surface of the braided portion adjacent the coil.

7. The medical insertion device of claim 1, wherein the lines are wound with a predetermined pick count.

8. The medical insertion device of claim 7, wherein the lines are wound in a locking braid pattern such that crossings of the lines occur at one of valleys of the coil, peaks of the coil and a combination of the valleys and peaks of the coil.

9. The medical insertion device of claim 1, wherein the line has one of a rectangular and circular cross-section.

10. The medical insertion device of claim 1, wherein a distal end of the elongated shaft is formed to engage a tissue-clipping device.

11. A medical insertion device, comprising:
an elongated shaft extending from a proximal end to a distal end and having flexibility sufficient for insertion through a working channel of an endoscope along a tortuous path, the elongated shaft including:
a coiled shaft portion extending from the proximal end to the distal end; and
a braided shaft portion positioned over the coiled shaft portion, the braided shaft portion formed of a plurality of lines braided together such that first and second ones of the lines intersect to enclose a predetermined angle therebetween, the angle being at least 25 degrees and less than 50 degrees, wherein each of the first and second ones of the lines includes at least one filament, a diameter of filaments of the first one of the lines being different from a diameter of filaments of the second one of the lines.

12. The medical insertion device of claim 11, wherein the lines are braided in an interlocking pattern.

13. The medical insertion device of claim 11, wherein the first one of the lines includes one of one two, three and four filaments and the second one of the lines includes one of one, two, three and four filaments.

14. The medical insertion device of claim 11, further comprising a plastic extrusion locking an orientation of the braided shaft portion relative to the coiled shaft portion.

15. The medical insertion device of claim 14, wherein the plastic extrusion is positioned on one of an outer surface of the braided shaft portion and an inner surface of the braided shaft portion adjacent the coiled shaft portion.

16. A method for deploying a medical device in a living body, comprising the steps of:
advancing a flexible member to a target position in a living body, the flexible member extending from a handle at a proximal end to a distal end sized and shaped for insertion to the target position in the living body and having a first channel extending longitudinally therethrough, the flexible member including a coil extending from the proximal end to the distal end and a braided portion positioned over a portion of the coil, the braided portion formed of a plurality of lines braided together such that first and second ones of the lines intersect to enclose a predetermined angle therebetween, the angle being at least 25 degrees and less than 50 degrees, wherein each of the first and second ones of the lines includes at least one filament, a diameter of filaments of the first one of the lines being different from a diameter of filaments of the second one of the lines;
rotating the handle to cause a corresponding rotation of the medical device connected to the distal end of the flexible member; and
performing a target medical procedure using the medical device.

17. The method according to claim 16, wherein the medical device is a tissue-clipping device.

* * * * *